United States Patent
Yamaguchi et al.

(10) Patent No.: US 6,569,412 B2
(45) Date of Patent: May 27, 2003

(54) TREATMENT COMPOSITION FOR DYED HAIR

(75) Inventors: Masakazu Yamaguchi, Tokyo (JP); Shintaro Totoki, Tokyo (JP); Makoto Iijima, Toyko (JP); Hajime Miyabe, Toyko (JP)

(73) Assignee: Kao Corporation, Tokyo (JP)

( * ) Notice: Subject to any disclaimer, the term of this patent is extended or adjusted under 35 U.S.C. 154(b) by 60 days.

(21) Appl. No.: 09/753,551

(22) Filed: Jan. 4, 2001

(65) Prior Publication Data
US 2001/0007160 A1 Jul. 12, 2001

(30) Foreign Application Priority Data

Jan. 7, 2000 (JP) ........................................ 2000-001999

(51) Int. Cl.$^7$ .................................................. A61K 7/06
(52) U.S. Cl. .................... 424/70.1; 424/70.2; 424/70.5; 424/70.19; 424/70.21; 424/70.22; 424/70.24
(58) Field of Search ............................. 424/70.1, 70.15, 424/70.2, 70.5, 70.19, 70.21, 70.22, 70.24; 8/406, 405, 431, 409; 562/410

(56) References Cited

U.S. PATENT DOCUMENTS

| | | | | |
|---|---|---|---|---|
| 4,314,807 A | * | 2/1982 | Grollier et al. ................. | 8/406 |
| 5,601,620 A | * | 2/1997 | Ishikawa ....................... | 8/405 |
| 5,750,099 A | | 5/1998 | Yoshihara et al. ........ | 424/70.17 |
| 5,865,855 A | * | 2/1999 | Doehling et al. .............. | 8/409 |
| 5,958,084 A | * | 9/1999 | Shibata et al. ................. | 8/408 |
| 5,972,044 A | * | 10/1999 | Braun et al. .................... | 8/405 |
| 6,020,522 A | * | 2/2000 | Ishii et al. .................. | 562/410 |
| 6,036,730 A | * | 3/2000 | Yoshida et al. ................. | 8/406 |
| 6,099,828 A | * | 8/2000 | Kajino et al. ............ | 424/70.15 |
| 6,156,077 A | * | 12/2000 | Shibata et al. ................. | 8/406 |
| 6,206,935 B1 | * | 3/2001 | Onitsuka et al. ............... | 8/431 |

FOREIGN PATENT DOCUMENTS

| | | |
|---|---|---|
| DE | 42 25 985 | 2/1994 |
| DE | 197 51 550 | 7/1999 |
| EP | 0 529 437 | 3/1993 |
| EP | 0 978 272 | 2/2000 |
| JP | 06-340521 | 12/1994 |
| JP | 9-20625 | 1/1997 |
| JP | 09-020625 | 1/1997 |
| JP | 10-182373 | 7/1998 |
| JP | 10-330229 | 12/1998 |

\* cited by examiner

Primary Examiner—Yogendra N. Gupta
Assistant Examiner—Eisa Elhilo
(74) Attorney, Agent, or Firm—Oblon, Spivak, McClelland, Maier & Neustadt, P.C.

(57) ABSTRACT

The present invention provides a treatment composition for dyed hair which effectively prevents color fading of the dyed hair, to thereby maintain the color of the dyed hair for prolonged periods. The composition contains the following components (A), (B), and (C):

(A) an organic solvent selected from among aromatic alcohols, lower alkylene carbonates, N-alkylpyrrolidones, and formamides;

(B) an organic carboxylic acid or a salt thereof; and (C) a lower alcohol, a polyhydric alcohol, or a lower alkyl ether of a polyhydric alcohol;

wherein the pH of the composition falls within the range of 1–6 inclusive, and the composition does not contain any dye. In use, the composition is applied to hair dyed with an acid-dye-type hair dye composition; and then the hair is left to stand for 5–30 minutes at 20–60° C., followed by washing.

11 Claims, No Drawings

TREATMENT COMPOSITION FOR DYED HAIR

TECHNICAL FIELD

The present invention relates to a hair treatment composition capable of effectively preventing color fading and bleeding of dyed hair to thereby maintain the color for a prolonged period of time. The invention also relates to a method for treating the dyed hair.

BACKGROUND ART

When hair is dyed with a hair dye composition of the acid-dye type, the composition is directly adsorbed onto strands of the hair due to the ionicity of the composition. Hair dye compositions of the acid-dye type (hereinafter may be referred to as acid-dye-type hair dye compositions) provide a broad range of color and exert negligible side effects on the hair and scalp, thereby permitting easy and safe use of the compositions by people susceptible to allergies and by pregnant women. As a result, acid-dye-type hair dye compositions have come to be widely used as replacements for oxidative hair dye compositions. However, in general, the problem with acid-dye-type hair dye compositions is that they exhibit poor color durability against shampooing. Several techniques for realizing improved color durability have heretofore been disclosed. For example, incorporation of hair-permeable organic solvents, such as benzyl alcohol, into a hair dye composition has been proposed. Also, there have been proposed a method which includes pretreatment of the hair with a composition containing a specific combination of an organic solvent and an organic acid (Japanese Patent Application Laid-Open (kokai) No. 10-182373), and a method employing a color fading prevention agent containing 2-hydroxybenzyl alcohol or phenylethylene glycol (Japanese Patent Application Laid-Open (kokai) No. 9-20625).

However, no such conventional means can satisfactorily prevent color fading in dyed hair that is repeatedly shampooed or repeatedly worked with treatment agents or hair styling agents. Also, since 2-hydroxybenzyl alcohol and phenylethylene glycol are high-melting-point compounds, they are difficult to incorporate into a hair dye composition in a consistent manner and may have a stimulatory effect or cause sensitivity, thus imposing limitations on their use.

In view of the foregoing, an object of the present invention is to provide a hair treatment composition which is endowed with improved dye fixation power, improved color durability against shampooing, and high safety.

Another object of the present invention is to provide a method for treating the hair with such a composition.

DISCLOSURE OF THE INVENTION

The present inventors have performed extensive research regarding the mechanism of removal and fading of dye that has been adsorbed onto the dyed hair strands, and have found that a composition comprising a specific combination of an organic solvent, an organic carboxylic acid or a salt thereof, and an alcohol and falling within a specific pH range effectively prevents fading of color of the dyed hair to thereby enable the hair to hold the dye color for a prolonged period of time, thus leading to completion of the invention.

Accordingly, the present invention provides a treatment composition for dyed hair which comprises the following components (A), (B), and (C):

(A) an organic solvent selected from among aromatic alcohols, lower alkylene carbonates, N-alkylpyrrolidones, and formamides;
(B) an organic carboxylic acid or a salt thereof; and
(C) a lower alcohol, a polyhydric alcohol, or a lower alkyl ether of a polyhydric alcohol;

wherein the pH of the composition falls within the range of 1–6 inclusive, and the composition is free of a dye.

The present invention also provides a method for treating the hair which comprises applying the above treatment composition to hair dyed with an acid-dye-type hair dye composition; leaving the dyed hair to stand for 5–30 minutes at 20–60° C.; and washing the hair.

BEST MODE FOR CARRYING OUT THE INVENTION

Component (A); i.e., an organic solvent, to be incorporated into the treatment composition for dyed hair (hereinafter may be referred to as the dyed-hair treatment composition) promotes permeation of an acidic dye or a similar substance into hair fibers. Among the aforementioned class of organic solvents, examples of the aromatic alcohols include benzyl alcohol, benzyloxyethanol, phenethyl alcohol, γ-phenylpropyl alcohol, cinnamyl alcohol, anise alcohol, p-methylbenzyl alcohol, α-α-dimethylphenethyl alcohol, α-phenyl ethanol, and phenoxy ethanol; examples of the lower alkylene carbonates include C2–C6 alkylene group-containing carbonates such as ethylene carbonate, propylene carbonate, and butylene carbonate; examples of the N-alkylpyrrolidones include N-methylpyrrolidone and N-ethylpyrrolidone; and examples of the formamides include N-cyclohexylformamide, N,N-dimethylformamide, and N-methylformamide.

Among the above-listed compounds serving as component (A), benzyl alcohol, benzyloxyethanol, and propylene carbonate are preferred to assure accelerated penetration of the composition into the hair fibers and fixation of the hair dye.

The above-listed compounds, which serve as component (A), may be used singly or in combination of two or more species. From the viewpoints of accelerated hair penetration and improved dye fixation, component (A) is preferably incorporated into the dyed-hair treatment composition in an amount of about 1 to about 50 wt. %, more preferably about 5 to about 45 wt. %, on the basis of the entirety of the composition.

Component (B); i.e., an organic calboxylic acid or a salt thereof, to be incorporated into the dyed-hair treatment composition, is preferably odorless and water soluble. Examples of such organic calboxylic acids or salts thereof include hydroxylic acids such as glycolic acid, lactic acid, citric acid, tartaric acid, and malic acid; keto acids such as levulinic acid; mono- or di-carboxylic acids such as acetic acid, maleic acid, and fumaric acid; and salts of any of these acids, such as sodium salts, which are soluble in the dyed-hair treatment composition of the present invention. In particular, glycolic acid, citric acid, malic acid, fumaric acid, lactic acid, and salts of these acids are preferred. These organic calboxylic acids or salts thereof may be used singly or in combination of two or more species.

To assure improvement in fixation rate for the hair dye, the amount of component (B) to be incorporated into the dyed-hair treatment composition is preferably about 1 to about 30 wt. %, more preferably about 3 to about 10 wt. %, on the basis of the entirety of the composition, the percentage being expressed in terms of organic carboxylic acid.

Examples of the lower alcohols serving as component (C) include C2–C6 linear or branched alcohols, and preferred examples include ethanol, isopropanol, n-propanol, and n-butanol.

Examples of the polyhydric alcohols serving as component (C) include alkylene glycols such as 1,3-butylene glycol, ethylene glycol, diethylene glycol, hexylene glycol, dipropylene glycol, triethylene glycol, and polyethylene glycol (M.W.: 200–5,000); and glycerols such as diglycerol and polyglycerol. Examples of lower alkyl ethers of the polyhydric alcohols—such ether compounds are sometimes referred to as carbitols—include monoethers of alkylene glycols, such as ethylene glycol monoethyl ether, ethylene glycol monoisopropyl ether, diethylene glycol monoethyl ether, diethylene glycol monobutyl ether, and triethylene glycol monoethyl ether glycerol. Of these, particularly preferred are 1,3-butylene glycol, diethylene glycol, hexylene glycol, dipropylene glycol, triethylene glycol, polyethylene glycol (M.W. : 200–1,000), and diethylene glycol monobutyl ether.

These compounds serving as component (C) may be used singly or as a mixture of two or more species, and to assure stability of the resultant composition, the amount of component (C) to be incorporated into the dyed-hair treatment composition is preferably about 5 to about 50 wt. %, more preferably about 10 to about 30 wt. %, on the basis of the entirety of the composition.

In addition to these components (A), (B), and (C), when C2–C5 hydroxyalkane sulfonic acid or a salt thereof—hereinafter may be referred to as component (D)—is also incorporated into the dyed-hair treatment composition of the present invention, even better effects can be obtained in terms of the prevention of color fading and the durability against washing.

Examples of C2–C5 hydroxyalkane sulfonic acids serving as component (D) include 2-hydroxyethane sulfonic acid, 3-hydroxypropane sulfonic acid, and 2-hydroxypropane sulfonic acid. Examples of the salts of the C2–C5 hydroxyalkane sulfonic acids include physiologically acceptable salts, such as ammonium salts, sodium salts, and potassium salts. The compound (D) is preferably 2-hydroxyethane sulfonic acid or a sodium salt thereof. Compound (D) is preferably incorporated into the dyed-hair treatment composition in an amount of about 0.1 to about 50 wt. %, more preferably about 1 to about 10 wt. % on the basis of the entirety of the composition.

The balance of the dyed-hair treatment composition of the present invention is water. The pH of the composition must fall within the range of 1 to 6, preferably 2 to 5, more preferably 2 to 4, all measured at 25° C., for reliably preventing color fading.

The pH can be adjusted by use of an organic carboxylic acid serving as component (B). Alternatively, the pH can be adjusted by conventionally employed pH regulators, such as hydrochloric acid, phosphoric acid, sodium salts of these acids, or alkali agents such as ammonia water, sodium hydroxide, potassium hydroxide, and organic amines.

The dyed-hair treatment composition of the present invention may further contain other optional components as needed. For example, the composition may contain a surfactant, silicone, higher alcohol, ester oil, animal or vegetable oil, amino acid, polypeptide, a viscosity modifier, a sensation improver, a humectant, a hair-growing/nourishing agent, an anti-oxidation agent, perfume, and/or a coloring agent. As the viscosity modifier, a water-soluble polymer is preferably used. Examples of the water-soluble polymer include natural gum, such as xanthan gum and guar gum, and its modified products; cellulose derivatives such as hydroxyethyl cellulose, methyl cellulose, and carboxymethyl cellulose; alginic acid derivatives such as sodium alginate and propylene glycol alginate; and synthesized polymers such as polyvinyl alcohol, polyvinyl pyrrolidone, and polyethylene glycols having a molecular weight over 5,000. Of these compounds, natural gums or their modified products, and cellulose derivatives are preferably used. Preferably, the amount of these compounds to be incorporated into the dyed-hair treatment composition is about 0.1 to about 5.0 wt. % on the basis of the entirety of the composition. There may also be used, along with the composition of the present invention, post-treatment agents for hair or textile fibers, such as tannic acid or similar substances, which are known to exhibit color fading prevention effect on human hair, wool, silk, nylon fiber, etc. that are dyed with acid-dye-type dye compositions.

The dyed-hair treatment composition of the present invention may take any form, such as a liquid, gel, cream, milky emulsion, spray, or foam.

In a preferable manner of use, the dyed-hair treatment composition of the present invention is applied to hair fibers which have been dyed with an acid-dye type hair dye composition, and the hair is left to stand for 5–30 minutes at 20–60° C. Subsequently, the composition is rinsed off by means of washing.

As used herein, the term "acid-dye-type hair dye composition" refers to any hair dye composition containing a so-called acid dye. In this connection, an acid dye is a dye compound having an acidic group (such as a hydroxyl group, a carboxyl group, or a sulfonic acid group), and through ionization in an aqueous solution, the dye moiety of the compound is transformed into an anion. Examples of the acid dye include, but are not limited to, Blue #1, Purple #401, Black #401, Orange #205, Red #201, Red #227, Red #106, Yellow #4, and Yellow #403. The composition of a typical acid-dye-type hair dye composition includes the components (A) through (C), or components (A) through (D), of the present invention and about 0.1 to about 10 wt. % of an acid dye.

The dyed-hair treatment composition may be applied to wet hair or dry hair. Also, the application may be performed immediately after hair-dyeing, or after some time has elapsed following hair dyeing. Repeated application of the composition of the present invention provides an even better color fading prevention effect.

In a more preferred manner of use, the hair is dyed with a conventional acid-dye type hair dye composition, and excess hair dye composition is washed off by shampooing, followed by towel-drying. Subsequently, the dyed-hair treatment composition of the present invention is applied thereto, and the hair is left to stand for 5–30 minutes at 20–60° C., preferably 20–45° C. Finally, the composition is rinsed off with water, or the hair is shampooed.

EXAMPLES

Working Examples 1 to 7

The dyed-hair treatment compositions shown in Table 1 were prepared, and the compositions were tested as described below for evaluation in terms of the color fading prevention of dyed hair and the durability against washing.

TABLE 1

| Components (wt. %) | Working Examples | | | | | | | Comparative Examples | | |
|---|---|---|---|---|---|---|---|---|---|---|
| | 1 | 2 | 3 | 4 | 5 | 6 | 7 | 1 | 2 | 3 |
| Benzyl alcohol | 10.0 | — | — | — | 10.0 | 10.0 | — | 10.0 | — | — |
| Benzyloxyethanol | — | 15.0 | — | 10.0 | — | — | 10.0 | — | 10.0 | — |
| Propylene carbonate | — | 5.0 | 25.0 | 15.0 | 10.0 | — | — | — | — | — |
| Malic acid | 5.0 | — | 2.5 | — | — | — | — | — | — | — |
| Lactic acid | — | 5.0 | 2.5 | 5.0 | 5.0 | 5.0 | 5.0 | 5.0 | — | 5.0 |
| Sodium hydroxide/HCl | S.A. | S.A. | S.A. | S.A. | S.A. | S.A. | S.A. | S.A. | S.A. | S.A. |
| Isopropanol | 5.0 | 5.0 | 5.0 | 5.0 | — | — | — | — | 20.0 | 20.0 |
| 1,3-Butylene glycol | — | — | — | — | — | 5.0 | 5.0 | — | — | — |
| Hexylene glycol | 10.0 | 5.0 | — | — | — | — | — | — | — | — |
| Polyethylene glycol 300 | — | — | 10.0 | 10.0 | 10.0 | — | — | — | — | — |
| Polyethylene glycol 400 | — | — | — | — | — | 10.0 | 10.0 | — | — | — |
| Polyethylene glycol 600 | — | 5.0 | — | — | 10.0 | — | — | — | — | — |
| Diethylene glycol monobutyl ether | — | — | — | 5.0 | — | — | — | — | 15.0 | — |
| Silicone (KF6005) | 1.5 | 1.5 | 1.5 | 1.5 | 1.5 | 1.5 | 1.5 | 1.5 | 1.5 | 1.5 |
| Hydroxy-ethyl cellulose | 2.0 | 2.0 | 2.0 | 2.0 | 2.0 | 2.5 | 2.5 | 2.0 | 2.0 | 2.0 |
| Perfume | 0.3 | 0.3 | 0.3 | 0.3 | 0.3 | 0.3 | 0.3 | 0.3 | 0.3 | 0.3 |
| Purified Water | Balance | Balance | Balance | Balance | Balance | Balance | Balance | Balance | Balance | Balance |

Adjusted with NaOH or HCL to pH3
S.A.: Suitable amount

Dyeing of the Hair with an Acid-Dye-Type Dye Composition

Human gray hair strands (1.0 g) were dyed with an acid-dye-type dye composition (1.0 g) having the following formula and washed with a shampoo. The hair strands were towel-dried to remove excessive water and the weight of the strands was adjusted to 1.3 g.

| Formula: | |
|---|---|
| 50 wt. % Citric acid | 5.0 wt. % |
| 48 wt. % Sodium hydroxide | 0.2 |
| 95 wt. % Ethanol | 8.0 |
| 1,3-Butylene glycol | 5.0 |
| Benzyloxyethanol | 10.0 |
| Xanthan gum | 1.8 |
| Orange #205 | 0.64 |
| Red No. 106 | 0.06 |
| Water | Balance |

Test for Evaluation of Color Fading
<Test Method 1>

Each of the dyed-hair treatment compositions (1.0 g) according to Working Examples 1 to 7 and Comparative Examples 1 to 3 was applied to a tress of dyed hair strands, and the hair strands were left to stand for 10 minutes at 20° C. or 45° C. Subsequently, the hair strands were rinsed and towel-dried to remove excessive water, to thereby adjust the weight of the hair tress to 1.3 g. A 10-fold diluted shampoo composition (1.0 g) was applied to the hair tress. The hair tress was allowed to stand for 5 minutes at 20° C., and squeezed to collect any colored water. A portion (0.2 mL) of the colored water was uniformly applied to a filter paper of 3 cm×3 cm. After the filter paper was sufficiently dried, the degree of fading of dyed color was visually assessed in terms of five ratings.
<Evaluation Standards>
  1: Almost no color fading
  2: Slight color fading
  3: Moderate
  4: Recognizable level of color fading
  5: Significant color fading The results are shown in Table 2.

TABLE 2

| | Working Examples | | | | | | | Comparative Working Examples | | |
|---|---|---|---|---|---|---|---|---|---|---|
| | 1 | 2 | 3 | 4 | 5 | 6 | 7 | 1 | 2 | 3 |
| Treatment at 20° C. | 2 | 1 | 1 | 1 | 2 | 2 | 1 | 4 | 3 | 4 |
| Treatment at 45° C. | 1 | 1 | 1 | 1 | 1 | 1 | 1 | 3 | 4 | 4 |

Test for Evaluation of Color durability Against Washing
<Test Method>

Each of the dyed-hair treatment compositions (1.0 g) according to Working Examples 1 to 7 and Comparative Examples 1 to 3 was applied to a tress of dyed hair strands, and the hair strands were left to stand for 10 minutes at 20° C. or 45° C. Subsequently, the hair strands were shampooed five, ten, or fifteen times, and the degree of color fading from the dyed hair strands was visually assessed in terms of five ratings.
<Evaluation Standards>
  1: Almost no color fading
  2: Slight color fading
  3: Moderate
  4: Recognizable level of color fading
  5: Significant color fading The results are shown in Table 3.

TABLE 3

| | | Working Examples | | | | | | | Comparative Working Examples | | |
|---|---|---|---|---|---|---|---|---|---|---|---|
| | | 1 | 2 | 3 | 4 | 5 | 6 | 7 | 1 | 2 | 3 |
| Treatment at 20° C. | After 5 shampooings | 1 | 1 | 1 | 1 | 1 | 1 | 1 | 3 | 3 | 3 |
| | After 10 shampooings | 2 | 1 | 1 | 2 | 2 | 1 | 2 | 4 | 3 | 4 |

TABLE 3-continued

|  |  | Working Examples | | | | | | | Comparative Working Examples | | |
|---|---|---|---|---|---|---|---|---|---|---|---|
|  |  | 1 | 2 | 3 | 4 | 5 | 6 | 7 | 1 | 2 | 3 |
| Treatment at 45° C. | After 15 shampooings | 2 | 2 | 2 | 2 | 2 | 2 | 2 | 5 | 5 | 5 |
|  | After 5 shampooings | 1 | 1 | 1 | 1 | 1 | 1 | 1 | 2 | 2 | 3 |
|  | After 10 shampooings | 1 | 1 | 1 | 1 | 1 | 1 | 1 | 3 | 3 | 3 |
|  | After 15 shampooings | 2 | 2 | 2 | 2 | 2 | 2 | 2 | 4 | 4 | 4 |

As is apparent from Tables 2 and 3, the dyed-hair treatment compositions of the present invention prevent bleeding of the dye from the hair, and thus enable the hair to hold the dye color for prolonged periods.

Working Examples 8 to 10

The dyed-hair treatment compositions shown in Table 4 were prepared.

TABLE 4

| | Working Examples | | |
|---|---|---|---|
| Components (wt. %) | 8 | 9 | 10 |
| Benzyl alcohol | 10.0 | — | — |
| Benzyloxyethanol | — | 10.0 | — |
| Propylene carbonate | — | — | 15.0 |
| Malic acid | 5.0 | — | — |
| Lactic acid | — | 5.0 | 5.0 |
| Sodium hydroxide | S.A. | S.A. | S.A. |
| Isopropanol | 5.0 | 5.0 | — |
| Hexylene glycol | 10.0 | — | — |
| Polyethylene glycol 300 | — | 10.0 | — |
| Diethylene glycol monobutyl ether | — | 5.0 | — |
| Sodium 2-hydroxyethanesulfonate | 10.0 | 5.0 | 5.0 |
| Silicone (KF6005) | 1.5 | 1.5 | — |
| Hydroxyethyl cellulose | 2.0 | 2.0 | — |
| Perfume | 0.3 | 0.3 | — |
| Purified water | Balance | Balance | Balance |

S.A.: Suitable amount

The amount of sodium hydroxide was adjusted so as to make the pH of the composition 3.

Dyeing of the Hair with an Acid-Dye-Type Dye Composition

Human gray hair strands (1.0 g) were dyed with either of the dye compositions (1.0 g) shown in Table 5 and containing acid dyes, and washed with a shampoo. The hair strands were towel-dried to remove excessive water and the weight of the strands was adjusted to 1.3 g.

TABLE 5

| Components (wt. %) | Hair dye composition A | Hair dye composition B |
|---|---|---|
| Lactic acid | 5.0 | 5.0 |
| 95% ethanol | 10.0 | 10.0 |
| Benzyloxyethanol | 10.0 | 10.0 |
| Xanthan gum | 1.5 | 1.5 |
| Sodium hydroxide | Suitable amount | Suitable amount |
| Silicone (KF6005) | 1.5 | 1.5 |
| Perfume | 0.2 | 0.2 |
| Purified water | Balance | Balance |
| Orange #205 | 0.65 | 0.1 |
| Black #401 | — | 0.2 |
| Purple #401 | — | 0.1 |
| Yellow #203 | — | 0.15 |
| Red #106 | 0.1 | — |
| Red #227 | — | 0.1 |

The amount of sodium hydroxide was adjusted so as to make the pH of the composition 3.

Test for Evaluation of Color Fading

<Test Method 2>

Each of the dyed-hair treatment compositions (1.0 g) according to Working Examples 8 to 10 and water (1.0 g; as Comparative Example 4) was applied to a tress of dyed hair strands, and the hair strands were left to stand for 5 minutes at 20° C. or 45° C. Subsequently, the hair strands were shampooed and towel-dried to remove excessive water, to thereby adjust the weight of the hair tress to 1.3 g. 1.0 g of a 2 wt. % aqueous solution of sodium polyoxyethylene lauryl ether sulfate was applied to the hair tress. The hair tress was allowed to stand for 5 minutes at 20° C., and squeezed to collect any colored water resulting from transfer of the color from the acid dye. A portion (0.2 mL) of the collected colored water was uniformly applied to a filter paper of 3 cm×3 cm. After the filter paper was dried, the L, a, and b values were measured by use of a calorimeter CR-200 (Minolta, Tokyo). The degree of coloring of the squeezed water was obtained as a ΔE value (i.e., the distance between the measured L, a, or b value and the corresponding L, a, or b value of unused filter paper) in a color space. The results are shown in Table 6.

TABLE 6

| | Working Examples | | | Comparative Examples |
|---|---|---|---|---|
| | 8 | 9 | 10 | 4 |
| Dyed with hair dye comp. A Treatment at 20° C. | 9.9 | 10.1 | 12.9 | 25.5 |
| Dyed with hair dye comp. A Treatment at 45° C. | 6.8 | 8.4 | 10.6 | 32.5 |
| Dyed with hair dye comp. B Treatment at 20° C. | 10.0 | 11.7 | 13.4 | 20.2 |
| Dyed with hair dye comp. B Treatment at 45° C. | 6.8 | 8.4 | 10.6 | 32.5 |

Test for Evaluation of Color durability Against Washing

The results of the test performed in a manner similar to the test for Working Example 1 are shown in Table 7.

TABLE 7

|  | Working Examples | | | Comparative Examples |
|---|---|---|---|---|
|  | 8 | 9 | 10 | 4 |
| Hair was dyed with hair dye comp. A Treatment at 20° C. | | | | |
| After 5 shampooings | 1 | 1 | 2 | 3 |
| After 10 shampooings | 2 | 1 | 2 | 4 |
| After 15 shampooings | 2 | 2 | 3 | 5 |
| Hair was dyed with hair dye comp. A Treatment at 45° C. | | | | |
| After 5 shampooings | 1 | 1 | 1 | 4 |
| After 10 shampooings | 1 | 1 | 2 | 5 |
| After 15 shampooings | 1 | 2 | 2 | 5 |
| Hair was dyed with hair dye comp. B Treatment at 20° C. | | | | |
| After 5 shampooings | 1 | 1 | 2 | 3 |
| After 10 shampooings | 2 | 2 | 2 | 4 |
| After 15 shampooings | 2 | 2 | 3 | 5 |
| Hair was dyed with hair dye comp. B Treatment at 45° C. | | | | |
| After 5 shampooings | 1 | 2 | 2 | 4 |
| After 10 shampooings | 2 | 2 | 3 | 4 |
| After 15 shampooings | 2 | 2 | 3 | 5 |

As is apparent from Tables 6 and 7, the dyed-hair treatment compositions of the present invention prevent bleeding of the dye from the hair, and thus enable the hair to hold the dye color for prolonged periods.

INDUSTRIAL APPLICABILITY

The dyed-hair treatment composition of the present invention effectively prevents removal of the dye that is adhered to hair fibers dyed with an acid-dye-type hair dye composition, to thereby maintain the color of the dyed hair for prolonged periods. Moreover, since the respective components are stable and hygienically safe, the composition can be used in a variety of forms such as gel, cream, milky emulsion, spray, or foam.

What is claimed is:

1. A treatment composition for dyed hair which comprises the following components (A), (B), (C), and (D):
    (A) an organic solvent selected from the group consisting of aromatic alcohols, lower alkylene carbonates, N-alkylpyrrolidones, and formamides;
    (B) an organic carboxylic acid or a salt thereof; and
    (C) a lower alcohol, a polyhydric alcohol, or a lower alkyl ether of a polyhydric alcohol; and
    (D) $C_2$–$C_5$ hydroxyalkane sulfonic acid or a salt thereof;
wherein the pH of the composition falls within the range of 1–6 inclusive, and the composition is dye-free.

2. The treatment composition for dyed hair according to claim 1, wherein the component (A) is selected from the group consisting of benzyl alcohol, benzyloxyethanol, and propylene carbonate, and the component (B) is selected from the group consisting of glycolic acid, citric acid, malic acid, fumaric acid, lactic acid, and salts of any of these acids.

3. The treatment composition for dyed hair according to claim 1, wherein the component (A) is contained in an amount of about 0.1 to about 50 wt. %, the component (B) is contained in an amount of about 1 to about 30 wt. %, the component (C) is contained in an amount of about 5 to about 50 wt. %, and the component (D) is contained in an amount of about 0.1 to about 50 wt. %.

4. A method for treating the hair which comprises applying a treatment composition for dyed hair according to claim 1 to hair dyed with an acid-dye-type hair dye composition; leaving the dyed hair to stand for 5–30 minutes at 20–60° C.; and washing the hair.

5. The treatment composition for dyed hair according to claim 2, wherein the component (A) is contained in an amount of about 0.1 to about 50 wt. %, the component (B) is contained in an amount of about 1 to about 30 wt. %, the component (C) is contained in an amount of about 5 to about 50 wt. %, and the component (D) is contained in an amount of about 0.1 to about 50 wt. %.

6. The treatment composition for dyed hair according to claim 3, wherein component (A) is contained in an amount of about 5 to about 45 wt. %, component (B) is contained in an amount of about 3 to about 10 wt. %, component (C) is contained in an amount of about 10 to about 30 wt. %, and component (D) is contained in an amount of about 1 to about 10 wt. %.

7. The treatment composition for dyed hair according to claim 5, wherein component (A) is contained in an amount of about 5 to about 45 wt. %, component (B) is contained in an amount of about 3 to about 10 wt. %, component (C) is contained in an amount of about 10 to about 30 wt. %, and component (D) is contained in an amount of about 1 to about 10 wt. %.

8. The treatment composition for dyed hair according to claim 1, wherein component (D) is 2-hydroxyethane sulfonic acid or a sodium salt thereof.

9. The treatment composition for dyed hair according to claim 1, wherein the pH of the composition is 2–5 inclusive.

10. The treatment composition for dyed hair according to claim 9, wherein the pH of the composition is 2–4 inclusive.

11. A method for treating the hair which comprises applying the treatment composition for dyed hair according to claim 1 to hair dyed with an acid-dye-type hair dye composition; leaving the dyed hair to stand for 5–30 minutes at 20–60° C.; and washing the hair.

* * * * *